(12) United States Patent
Colella

(10) Patent No.: US 10,272,186 B2
(45) Date of Patent: *Apr. 30, 2019

(54) WIRE SCAFFOLD DEVICE FOR VENTRICULAR ASSIST DEVICE

(71) Applicant: HeartWare, Inc., Miami Lakes, FL (US)

(72) Inventor: Jeff Colella, Framingham, MA (US)

(73) Assignee: HeartWare, Inc., Miami Lakes, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/956,019

(22) Filed: Apr. 18, 2018

(65) Prior Publication Data

US 2018/0228957 A1 Aug. 16, 2018

Related U.S. Application Data

(63) Continuation of application No. 14/339,801, filed on Jul. 24, 2014, now Pat. No. 9,968,719.

(60) Provisional application No. 61/860,074, filed on Jul. 30, 2013.

(51) Int. Cl.
| | |
|---|---|
| *A61M 1/12* | (2006.01) |
| *A61M 1/10* | (2006.01) |
| *A61F 2/848* | (2013.01) |

(52) U.S. Cl.
CPC .............. *A61M 1/122* (2014.02); *A61F 2/848* (2013.01); *A61M 1/101* (2013.01); *A61M 1/1008* (2014.02); *A61M 1/1012* (2014.02); *A61M 1/125* (2014.02)

(58) Field of Classification Search
CPC ................................ A61M 1/122; A61F 2/848

USPC .......................................................... 600/16
See application file for complete search history.

(56) References Cited

U.S. PATENT DOCUMENTS

| | | | |
|---|---|---|---|
| 6,136,025 A | 10/2000 | Barbut et al. | |
| 8,641,594 B2 | 2/2014 | LaRose et al. | |
| 8,657,873 B2 | 2/2014 | Khairkhahan et al. | |
| 8,690,749 B1 | 4/2014 | Nunez | |
| 9,968,719 B2 * | 5/2018 | Colella | A61M 1/122 |
| 2002/0026944 A1 | 3/2002 | Aboul-Hosn et al. | |

(Continued)

OTHER PUBLICATIONS

International Search Report and Written Opinion dated Oct. 24, 2014 for corresponding International Application No. PCT/US2014/048572; International Filing Date: Jul. 29, 2014 consisting of 11-pages.

*Primary Examiner* — Carl H Layno
*Assistant Examiner* — Jon Eric C Morales
(74) *Attorney, Agent, or Firm* — Christopher & Weisberg, P.A.

(57) ABSTRACT

A ventricular assist system includes a ventricular assist device ("VAD") and an expandable stent. The VAD may include a pump and an inlet element defining an inlet opening communicating with the pump, the inlet element being adapted for positioning with the inlet opening disposed within a ventricle of a heart when the system is in an operative condition. The expandable stent may be adapted for positioning within the ventricle when the system is in the operative condition. The pump may be operated to draw blood from the ventricle and return the blood to the artery, and a wall of the ventricle may be held away from the inlet opening with the stent. The stent may be passed through a channel in the ventricular assist device while the stent is in a collapsed condition.

15 Claims, 14 Drawing Sheets

(56) References Cited

U.S. PATENT DOCUMENTS

| | | |
|---|---|---|
| 2007/0134993 A1 | 6/2007 | Tamez et al. |
| 2009/0112312 A1 | 4/2009 | LaRose et al. |
| 2009/0203957 A1 | 8/2009 | LaRose et al. |
| 2010/0022939 A1 | 1/2010 | Schima et al. |
| 2010/0249489 A1 | 9/2010 | Jarvik |
| 2010/0268017 A1 | 10/2010 | Siess |
| 2011/0124950 A1 | 5/2011 | Foster |
| 2011/0152999 A1 | 6/2011 | Hastings et al. |
| 2011/0184224 A1 | 7/2011 | Garrigue |
| 2012/0143141 A1 | 6/2012 | Verkaik et al. |
| 2012/0172655 A1 | 7/2012 | Campbell et al. |

\* cited by examiner

WIRE SCAFFOLD DEVICE FOR VENTRICULAR ASSIST DEVICE

CROSS-REFERENCE TO RELATED APPLICATIONS

This application is a continuation of U.S. patent application Ser. No. 14/339,801 filed Jul. 24, 2014, now U.S. Pat. No. 9,968,719, which application is related to and claims priority from Provisional Patent U.S. Patent Application Ser. No. 61/860,074, filed Jul. 30, 2013, the entirety of all of which are incorporated herein by reference.

BACKGROUND

The present disclosure relates to ventricular assist devices ("VADs"), to components useful in such devices, and to methods of using the same.

In certain disease states, the heart lacks sufficient pumping capacity to meet the needs of the body. This inadequacy can be alleviated by providing a mechanical pumping device, such as a VAD, to supplement the pumping action of the heart. Considerable effort has been devoted to providing a VAD which can be implanted and which can remain in operation for months or years to keep the patient alive while the heart heals, or which can remain in operation permanently or until a suitable donor heart becomes available if the heart does not heal.

A VAD is typically connected to the heart, most commonly to the left ventricle. For example, a VAD may include a pump which is installed in the body outside of the heart. The VAD may have an inlet cannula connected to the interior of the left ventricle and connected to the intake of the pump. The VAD may also include an outlet tube connected between the outlet of the pump and the aorta. Once connected, the VAD and the heart both pump blood from the left ventricle to the aorta. Some VADs may include a fluid intake or inlet within a chamber of the heart, such within the left ventricle. For example, U.S. Patent Publication No. 2009/0203957, the disclosure of which is hereby incorporated by reference herein, discloses a VAD with an inlet positioned within the left ventricle.

With such systems, depending on the particular positioning of the inlet, the operating parameters of the VAD, and the anatomy of the patient, a situation may arise in which heart tissue is pulled into the pump inlet. For example, a wall of the ventricle, the papillary muscles, or chordae tendinae may be sucked partially into the inlet. In other situations, such as when there is relatively little volume of fluid in the left ventricle, the walls of the left ventricle may be caused to partially collapse due to forces caused by the pump. Such a situation may be described as a suction condition. The scenarios described above may cause the pump to malfunction and may cause injury to the patient.

Patients with heart failure may have reduced left ventricular diameters that reduce the ability of the heart to fill during diastole. For example, some patients may have conditions such as hypertrophic cardiomyopathy in which walls of the heart become thick and rigid, or diastolic dysfunction in which the ventricle does not relax properly during diastole. In these patients, the ventricle may not fill with as much blood as in a healthy heart. Using existing VADs in patients with these types of conditions may be difficult.

BRIEF SUMMARY

One aspect of the present disclosure provides a ventricular assist system including a VAD and an expandable stent. The VAD may include a pump and an inlet element defining an inlet opening communicating with the pump, the inlet element being adapted for positioning with the inlet opening disposed within a ventricle of a heart when the system is in an operative condition. The expandable stent may be adapted for positioning within the ventricle when the system is in the operative condition. The system may also include a mounting that secures a part of the stent in position relative to the inlet element when the stent is positioned within the ventricle. The mounting may include an anchor element configured for attachment to the heart and the inlet element and the stent may be secured to the anchor element with the system is in the operative condition. The anchor element may include a channel extending therethrough. A one-way valve may be positioned at least partially within the channel. The system may include a sealing element configured to be positioned within the channel proximal to the one-way valve to seal the channel. The channel may have a diameter and the stent may have a collapsed condition and an expanded condition, the diameter of the channel being adapted to allow the stent to pass through the channel when the stent is in the collapsed condition. The anchor element may include a ring. The anchor element may include a substantially cylindrical member configured to be mounted to the heart at various positions along a length of the substantially cylindrical member. The stent may include a plurality of struts, the struts having inner ends and outer ends, the inner ends being disposed adjacent one another and the outer ends extending away from one another when the stent is in an expanded condition. The stent may be substantially cylindrical when in the expanded condition. The stent may be formed of a braided mesh.

Another aspect of the present disclosure includes a method of installing a ventricular assist device in a subject. The method may include mounting the ventricular assist device to the subject so that an inlet opening of an inlet element is disposed within a ventricle of the heart and the inlet opening communicates with a pump. The method may also include positioning an outflow cannula so that the outflow cannula communicates with the pump and with an artery, and positioning a stent in the ventricle at least partially upstream of the inlet of the pump. The pump may be operated to draw blood from the ventricle and return the blood to the artery, and a wall of the ventricle may be held away from the inlet opening with the stent. The stent may be passed through a channel in the ventricular assist device while the stent is in a collapsed condition. The step of passing the stent through the channel in the ventricular assist device may include passing the stent through a one-way valve positioned at least partially within the channel. The stent may be transitioned from the collapsed condition to an expanded condition. The channel may be sealed with a sealing element.

DETAILED DESCRIPTION

As used herein, the words "proximal" and "distal" denote directions and ends of the device and components. When referring the VAD or components thereof, the term "proximal" refers to the direction toward the surgeon or other operating room personnel during installation of the device and the term "distal" has the opposite meaning. Furthermore, when referring to the VAD or component thereof, the term "upstream" or "inflow" refers to a direction opposite the flow of blood in the VAD when operating as intended, while the term "downstream" or "outflow" refers to a direction with the flow of blood in the VAD when operating as intended.

Figure 1:
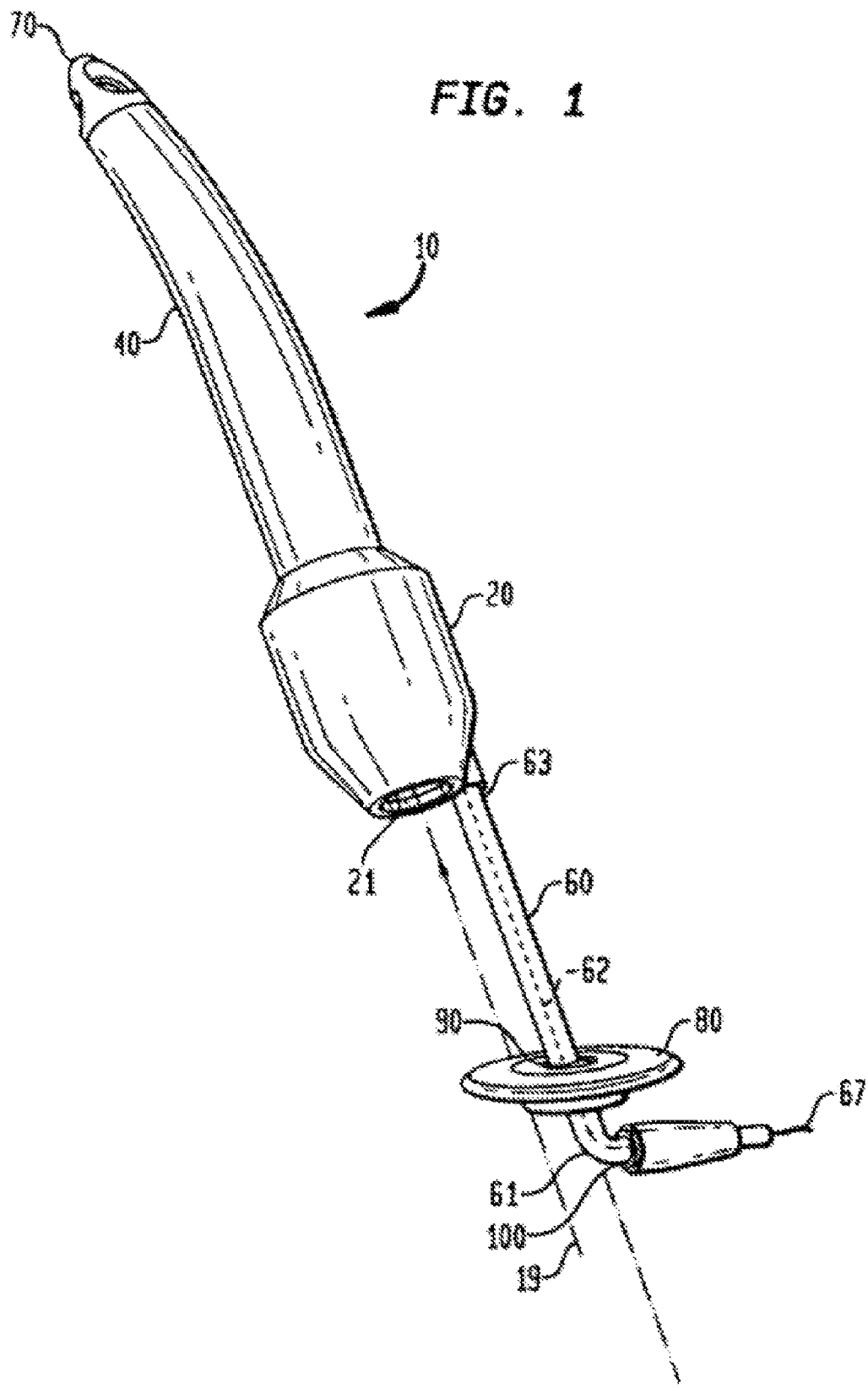
FIG. 1 is a diagrammatic perspective view of a ventricular assist device.
Figure 2:
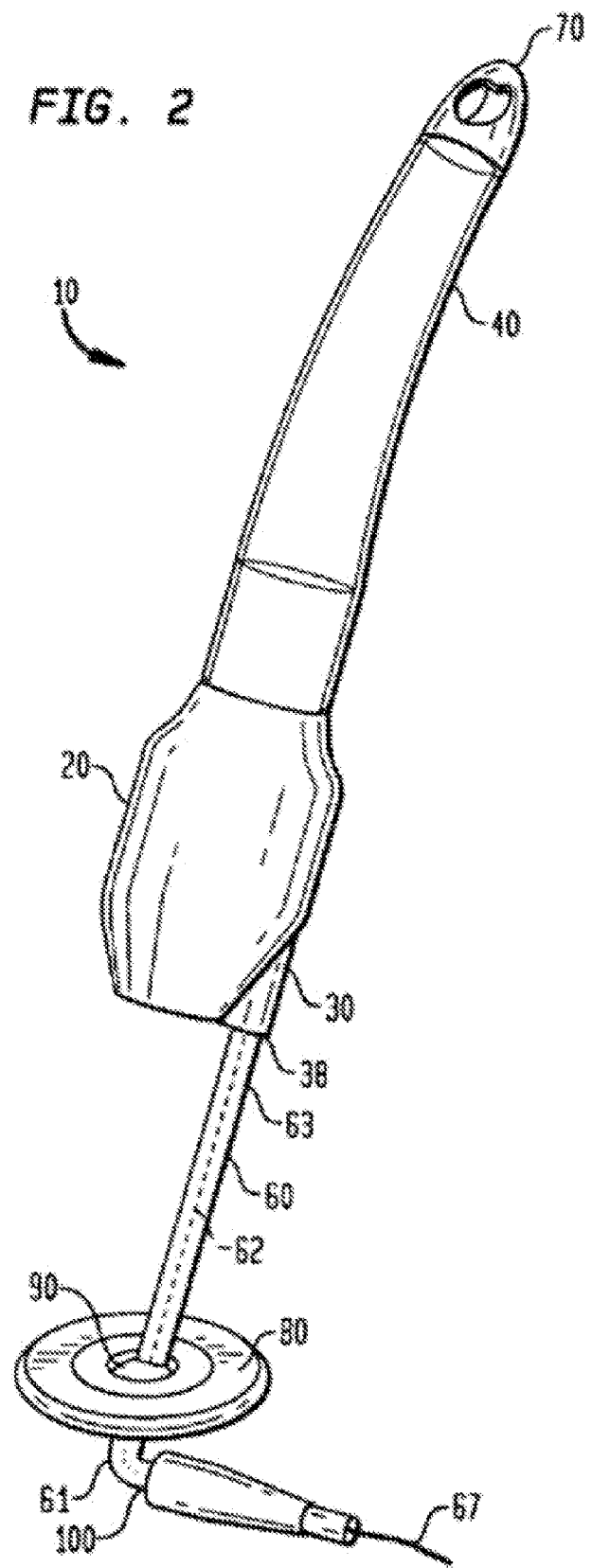
FIG. 2 is diagrammatic perspective view of the device of FIG. 1 from a different perspective.

Referring to the drawings, wherein like reference numerals refer to like elements, there is shown in FIGS. 1-2, an embodiment of a VAD 10. VAD 10 may include four sections including a pump 20, an outflow cannula 40, a rigid elongate member 60, and an anchoring element, such as ring 80.

Figure 3:
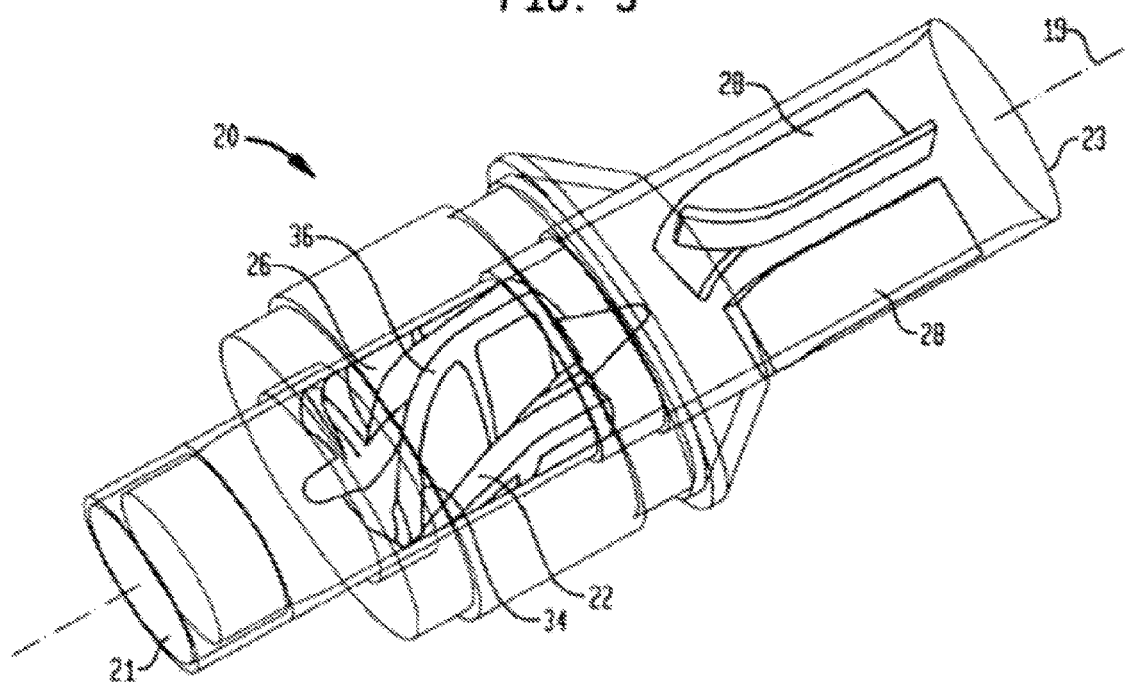
FIG. 3 is a perspective view of a pump of the device of FIG. 1.

One embodiment of pump 20 is shown in greater detail in FIG. 3. Pump 20 may be an axial flow pump having an inlet element 21 at an upstream position and an outlet 23 at a downstream position, the inlet 21 and outlet 23 arranged along an axis 19 referred to herein as the pump axis. The pump 20 may include an axial bore defined by a tubular housing 22 which extends between the inlet 21 and the outlet 22. Housing 22 may formed from biocompatible materials such as ceramics and metals such as titanium. The materials used for those portions of the housing 22 disposed inside the motor stator (discussed below) desirably are non-magnetic dielectric materials such as ceramics.

A motor stator may be disposed around the outside of tubular housing 22. The motor stator is arranged to provide a rotating magnetic field. Preferably, the motor stator contains both magnetic laminations and wire coils (not shown). Electrical current may be passed sequentially through the wire coils to produce the rotating electromagnetic field. The motor stator may be a conventional slotted or slotless design or may utilize an annular or toroidal design.

A rotor 26 may be disposed within the axial bore in alignment with the motor stator. Rotor 26 may be formed from a unitary piece of a magnetizable, biocompatible platinum-cobalt or platinum-cobalt-boron alloy. The rotor 26 may have a central axis coincident with pump axis 19, and may include a plurality of blades 34 projecting outwardly from such axis and curving around the axis in a generally helical pattern having a pitch angle which varies along the axial length of the rotor 26. The blades 34 may define flow channels 36 between them. Blades 34 may be configured so that their circumferential surfaces act as hydrodynamic bearings. Multiple hydrodynamic bearing surfaces may be provided on each blade, spaced along the axial length of the rotor 26, for greater hydrodynamic stability during operation. These rotor blades 34 may be magnetized for magnetic coupling to the motor stator. The number of rotor blades 34 is preferably either two or four for symmetry of magnetic poles. The rotor blades 34 impel blood within the housing 22 axially, toward the outlet 23.

The features of the rotor 26 and motor stator may be generally as shown in U.S. Patent Publication No. 2009/0112312 ("the '312 Publication"), the disclosure of which is hereby incorporated by reference herein. However, pump 20 typically is larger than a pump intended for positioning within an artery described in the '312 Publication. As an alternative to the unitary magnetic rotor 26 discussed above, a conventional rotor design involving placement of magnets sealed within a rotor formed from non-magnetic material may be used.

The pump may also include diffuser blades 28 mounted within housing 22 downstream from rotor 26, between the rotor 26 and the outlet 23. As best seen in FIG. 3, each diffuser blade 28 may be generally in the form of a plate-like vane secured to the housing 22 and projecting radially into the axial bore from the wall of the housing 22. The upstream ends of the diffuser blades 28, closest to rotor 26, may curve in a circumferential direction around the axis 19. The direction of curvature of the diffuser blades 28 may be opposite to the direction of curvature of the rotor blades 26. Preferably, the number of diffuser blades 28 is unequal to the number of rotor blades 34, and the number of diffuser blades 28 is not an integral multiple or divisor of the number of pump blades. Thus, where the rotor 26 has an even number of blades 34, the pump 20 desirably has an odd number of diffuser blades 28, such as three or five diffuser blades 28. This arrangement may help to maximize the stability of the rotor 26 and minimize vibration in operation of the pump 20. However, it should be understood that two, four, or more than five diffuser blades 28 may be utilized. During operation, the blood passing downstream from the rotor 26 has rotational momentum imparted by the rotor 26. As the blood encounters the diffuser blades 28, this rotational momentum is converted to axial momentum and pressure head. Thus, the diffuser blades 28 serve to reclaim the energy used to create the rotational motion and convert that energy to useful pumping work. In this embodiment, the diffuser blades 28 are not attached to one another at the axis. This arrangement conserves space within the axial bore, and thus maximizes axial flow.

Pump 20 may include an exterior shroud surrounding the housing 22 and motor stator. The shroud may be formed from a biocompatible metal such as titanium, a ceramic, or a biocompatible polymer. Exterior thromboresistant coatings may also be utilized to improve hemocompatibility. The shroud may define a first attachment portion 30 at the proximal or upstream end of the housing, near inlet 21. The first attachment portion 30 (FIG. 2) may have a recessed cavity 38 which extends into the shroud in a direction parallel to pump axis 19 but offset from the pump axis.

The apparatus may also include an elongate member 60 which has a proximal end 61, a distal end 63 and a bore 62 therethrough. Preferably, elongate member 60 has an axis along its direction of elongation which axis is parallel to the axis 19 of the pump body but offset from axis 19 in a direction transverse to both axes. Merely by way of example, elongate member 60 may be a tube formed from titanium or other biocompatible metal. Member 60 desirably is substantially rigid. That is, the member desirably is rigid enough to maintain the pump 20 in position, with no substantial movement relative to the ring 80 under the loads normally applied to the system while the system is in place within the heart. Elongate member 60 may include a spherical ball 90 mounted along the length thereof, remote from the distal end 63. Ball 90 may be fixedly attached to member 60 as, for example, by welding.

The distal end 63 of member 60 is received in recess 38 of first attachment portion 30 of the pump 20. Preferably, the distal end of member 60 is joined to the attachment portion of the pump by a permanent, fluid-tight connection as, for example, by welding member 60 to the pump shroud. Electrical power wiring 67 extends from the motor stator through bore 62 of member 60 and out of the member through a fitting 100 at the proximal end of the member. Preferably, there is a fluid-tight feedthrough (not shown) at fitting 100, at the connection between the distal end 63 and the attachment portion 30 of the pump 20, or both. The electrical wiring 67 extends out of the fitting 100 to a source of electrical power (not shown) external to the body of the patient or implanted within the body of the patient.

An outflow cannula 40 of extends distally from a distal end of pump 20 in the downstream direction. Outflow cannula 40 may be generally in the form of a hollow tube having a proximal end attached to pump 20 and communicating with the outlet 23 of the pump 20. The outflow cannula may have a tip 70 at its distal or outflow end.

Preferably, outflow cannula 40 is a single molded polymer piece made of thermoplastic polyurethanes (segmented and/or copolymerized with silicone, polycarbonate-urethanes, polyether-urethanes, aliphatic polycarbonate, or other additives), silicone, polycarbonate-urethanes, polyether-urethanes, aliphatic polycarbonate, silicone material with or without catalyst metals and possibly sulfonated styrenic polymers. Preferably, outflow cannula 40 may be cast with or without titanium wire structures for bend enhancement properties and non-invasive visualization of a catheter typically under x-ray or fluoroscopy. The outflow cannula 40 may contain barium sulfate or other minerals, or metallic marker bands to provide landmark location visualization by fluoroscopic, CAT or other radiological techniques during or after implantation in the patient.

Outflow cannula 40 may be straight or bent and desirably has an appropriate stiffness and hardness to accommodate the native heart and aortic root geometry and also to have non-traumatic contact with tissues. The diameter of the outflow cannula 40 may be tapered from pump housing 22 to a smaller diameter near the distal end of the outflow cannula 40. The distal end of the outflow cannula 40 may project through the aortic valve when the apparatus is implanted in a patient. A cannula which tapers in diameter towards its distal end may provide relatively low flow resistance due to its comparatively large diameter at the proximal end, and may also provide a desirable small diameter portion at the aortic valve. The small-diameter portion at the aortic valve helps to minimize aortic valve insufficiency, e.g. retrograde flow through the valve due to poor sealing of the tri-leaflets around the cannula. Desirably, the outflow cannula 40 is round in cross-section, at least in the region near tip 70 which may extend through the aortic valve when implanted. A round cross-sectional shape also minimizes aortic valve insufficiency.

The tip 70 of outflow cannula 40 may have any one of various shapes and geometries. For example, as shown, tip 70 has a circumferential surface which tapers inwardly toward the axis of the outflow cannula 40 in the distal direction, and thus converges toward the distal extremity of the outflow cannula 40. The distal surface of the tip 70 may define a smooth, dome-like shape at the distal extremity of the tip 70. A plurality of openings may extend through the circumferential surface of the tip 70 and communicate with the interior bore of the outflow cannula 40. When blood is discharged through these openings, the flow has a radial component which may provide a hydrodynamic self-centering force for cannula 40. The centering action may further minimize aortic valve insufficiency. Moreover, even if the cannula tip 70 is resting against an arterial wall, the plural openings spaced around the circumference of the tip 70 will still provide good blood flow. This tip geometry and other tip geometries are described in more detail in U.S. Patent Publication Nos. 2009/0203957 and 2010/0022939, the disclosures of which are both hereby incorporated by reference herein.

In this embodiment, the device 10 also includes an anchoring element in the form of a ring 80. Preferably, ring 80 is adapted for mounting adjacent the apex of the patient's heart by sewing around a perimeter of ring 80 to tissue along a wall of the patient's heart. For example, ring 80 may be a metallic structure having a peripheral flange with numerous holes for sewing or stapling the ring to the heart wall. The periphery of ring 80 may be covered with a fabric material such as for example polyester material, expanded polytetrafluoroethylene, felt or the like for promoting tissue growth over the ring to further secure the ring in place. U.S. Patent Publication No. 2007/0134993 describes ring components in more detail and is herein incorporated by reference herein.

Ring 80 preferably includes a spherical socket adapted to engage the spherical ball 90 of elongate member 60 such that ring 80 is pivotally or polyaxially mounted to elongate member 60 remote from pump 20. In the embodiment depicted, the pivotable connection between the ring 80 and the ball may be a permanent connection formed during manufacture. For example, ball 90 may be entrapped between elements of the ring 80 which are permanently connected to one another during manufacture. Ring 80 may be configured to align to the heart wall but can also allow for rotational movement to accommodate the native heart movement.

Figure 4:
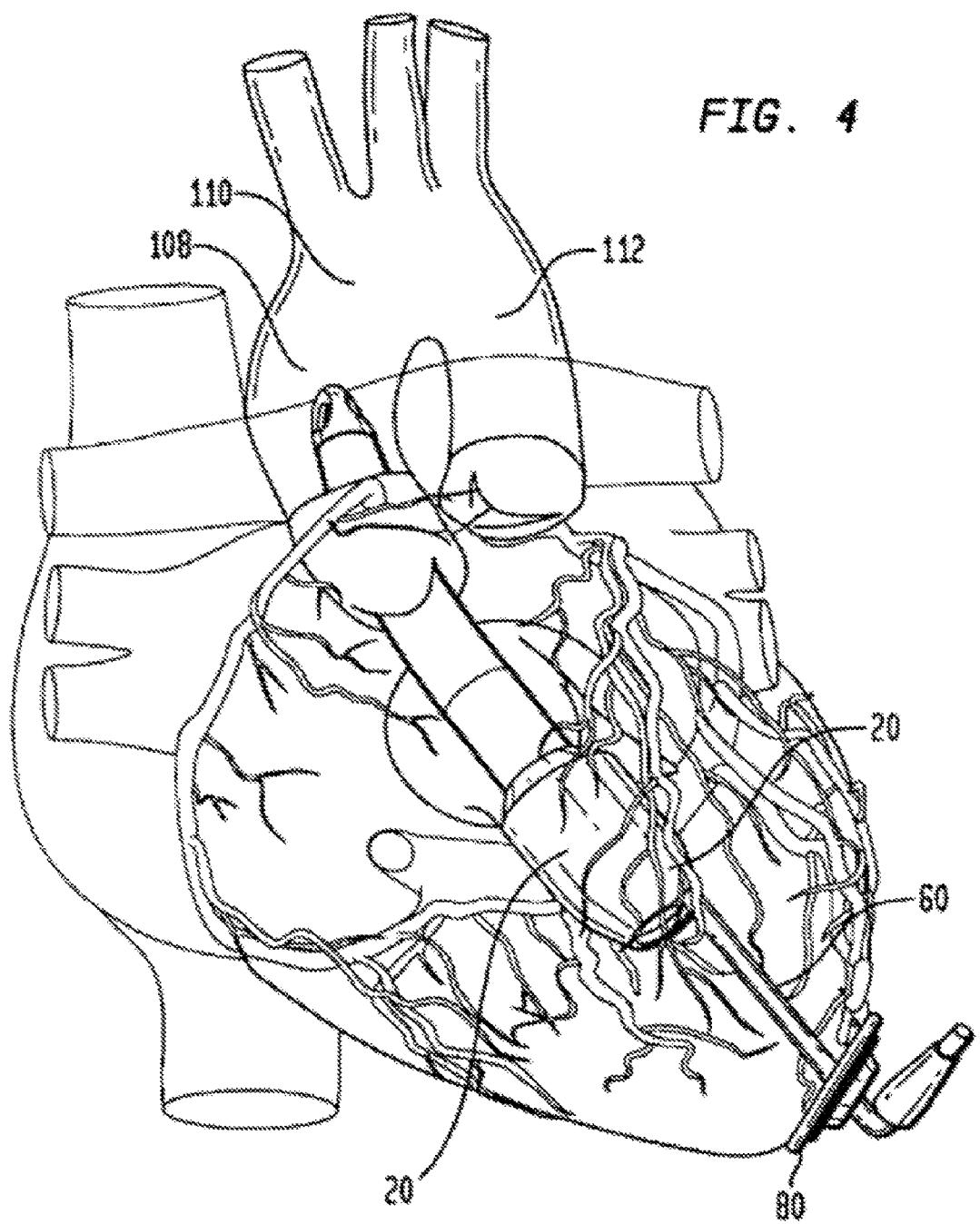
FIG. 4 is a diagrammatic view of the device of FIG. 1 in an installed condition, in conjunction with the certain structures of the heart.

In a method of implantation, the VAD 10, including the ring 80, member 60, pump 20 and outflow cannula 40 is provided as a pre-assembled unit. The surgeon gains access to the heart, preferably using a left subcostal or left thoracotomy incision exposing the left ventricular apex. A pledgeted purse string suture is then applied to the epicardium circumferentially over the pump insertion site. A slit incision or an incision in the form of a cross or X, commonly referred to as a "crux" incision, is made through the apex of the heart into the interior of the left ventricle using a cutting instrument such as a scalpel. Pump 20, member 60, and outflow cannula 40 are then inserted through the crux incision or slit incision and positioned within the left ventricle so that cannula 40 extends through the aortic valve into the aorta and an inlet opening of inlet element 21 of pump 20 is positioned within the left ventricle. Ring 80 is positioned on the outside of the heart as depicted in FIG. 4. Proper placement of the components can be verified by fluoroscope or other imaging technique. After placement, the pump can be started by applying electrical power from the external or implantable power source, and proper outflow may be verified using echocardiography. After outflow is verified, crux incision is closed around member 60, as by suturing, and ring 80 is secured to the exterior of the cardiac wall. It should be noted that the ring 80 may alternately be mounted to the heart prior to performing the incision.

As shown in FIG. 4, in the implanted condition, ring 80 is mounted adjacent the apex of the subject's heart. Ring 80 and pump 20 are connected to elongate member 60 remote from one another so that rigid elongate member 60 maintains pump 20 in position relative to ring 80. This maintains the pump and outflow cannula 40 in position relative to the heart.

The aortic valve is one of the atrioventricular valves of the heart. It lies between the left ventricle and the aorta. The ascending aorta 108 is a portion of the aorta commencing at the upper part of the base of the left ventricle. The aortic arch 110 also known as the transverse aorta begins at the level of the upper border of the second sternocostal articulation of the right side, and runs at first upward, backward, and to the left in front of the trachea. It is then directed backward on the left side of the trachea and finally passes downward on the left side of the body of the fourth thoracic vertebra, at the lower border of which it becomes continuous with the descending aorta 112.

Figure 9:
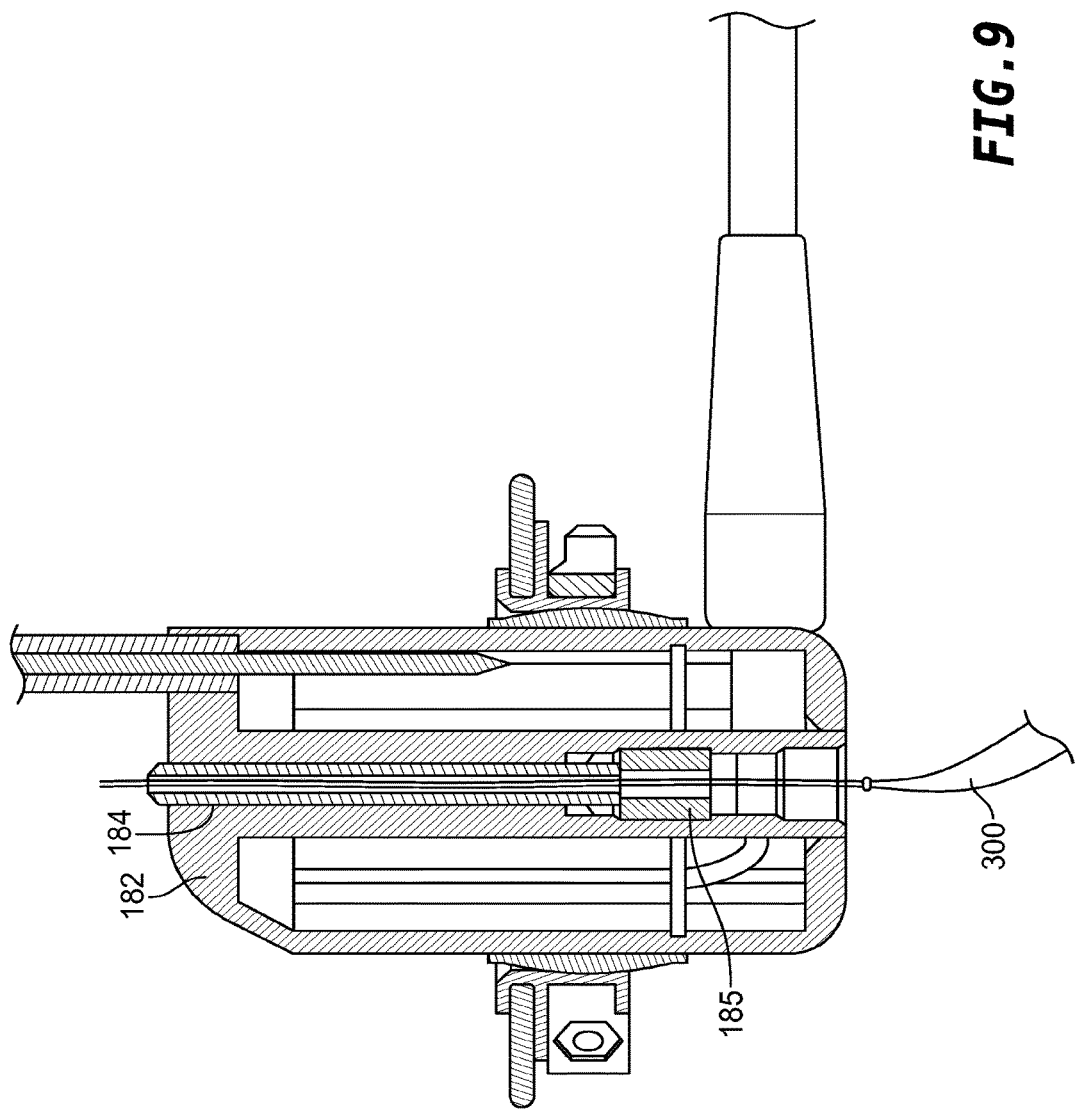
FIG. 9 is an enlarged cross-sectional view of a catheter inserted into the device of FIG. 5.

When the device is in the implanted condition shown in FIG. 9, the outflow cannula 40 projects through the aortic valve into the ascending aorta, but preferably terminates proximal to the arch 110 of the aorta. Thus, tip 70 of cannula 40 is preferably disposed distal to the aortic valve of the subject's heart, but the distal extremity of the tip is proximal to the aortic arch. This position of the outflow cannula 40 is advantageous in that it minimizes contact between the outflow cannula and the walls of the aorta, and thus minimizes trauma and thrombogenesis. The secure positioning of the pump 20 and outflow cannula 40 relative to the heart, provided by ring 80 and member 60, help to allow positioning of the cannula tip just distal to the aortic valve. Because the device is securely held in place within the heart, there is little or no possibility that movement of the cannula relative to the heart will allow the tip to move proximally, into the ventricle.

In the implanted or operative condition, the axis 19 of the pump extends near the apex of the heart, and the inlet opening of the inlet element 21 of the pump 20 is disposed inside the left ventricle and is aimed generally in the direction toward the apex of the heart. The length of elongate member 60 is such that the inlet 21 of pump 20 is remote from the aortic valve. This position and orientation provide certain advantages. Fibrous structures of the aortic valve, just proximal to the opening of the valve, do not get sucked into the inlet of pump 20. Moreover, the inlet 21 of the pump 20 will preferably not be occluded by the ventricular wall or the interventricular septum of the heart. However, occlusion of the inlet 21 by the ventricular wall or septum may still be possible, particularly in certain patient populations. In addition, a suction condition may still occur.

Figure 5:
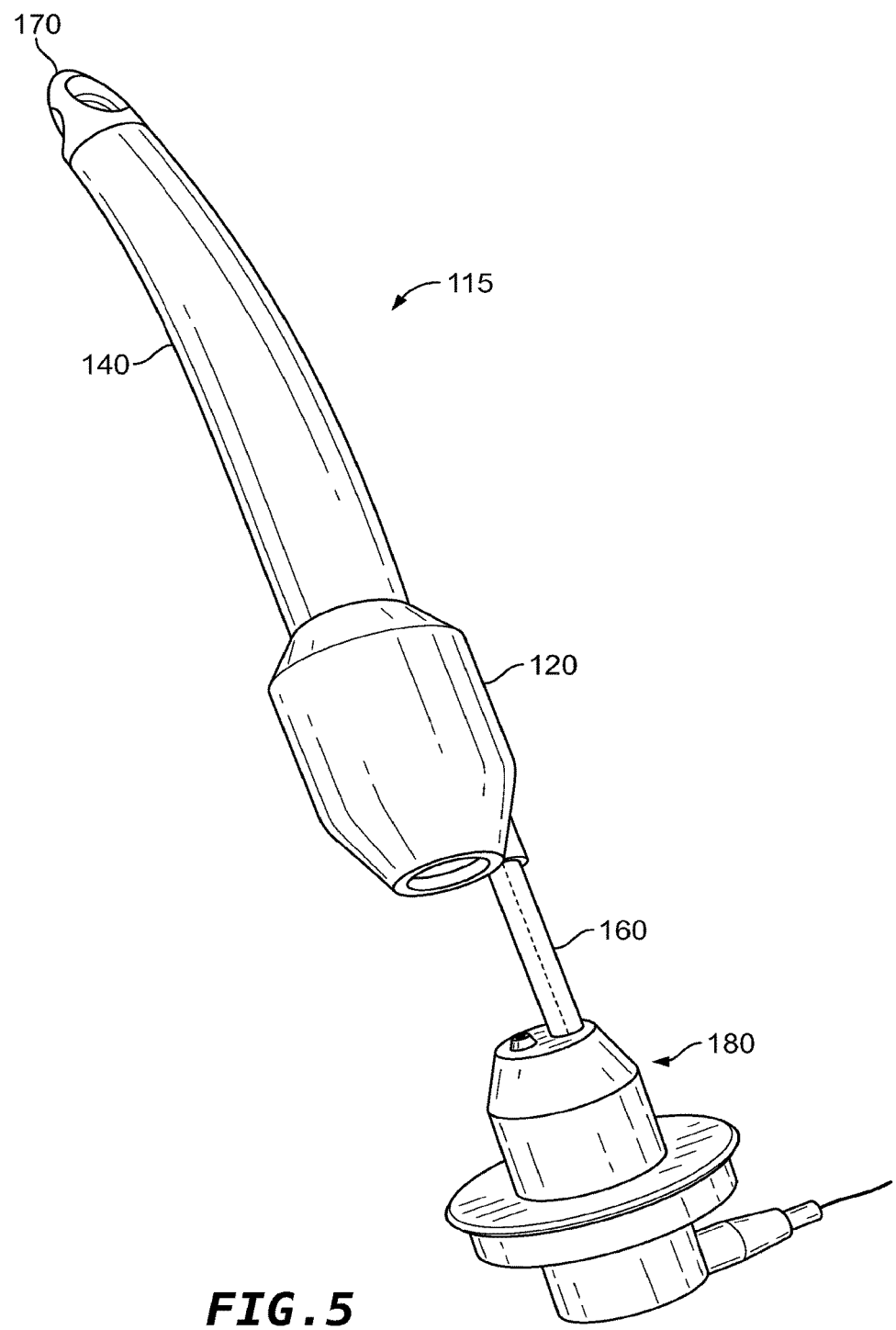
FIG. 5 is a diagrammatic perspective view of another embodiment of a ventricular assist device.
Figure 6:
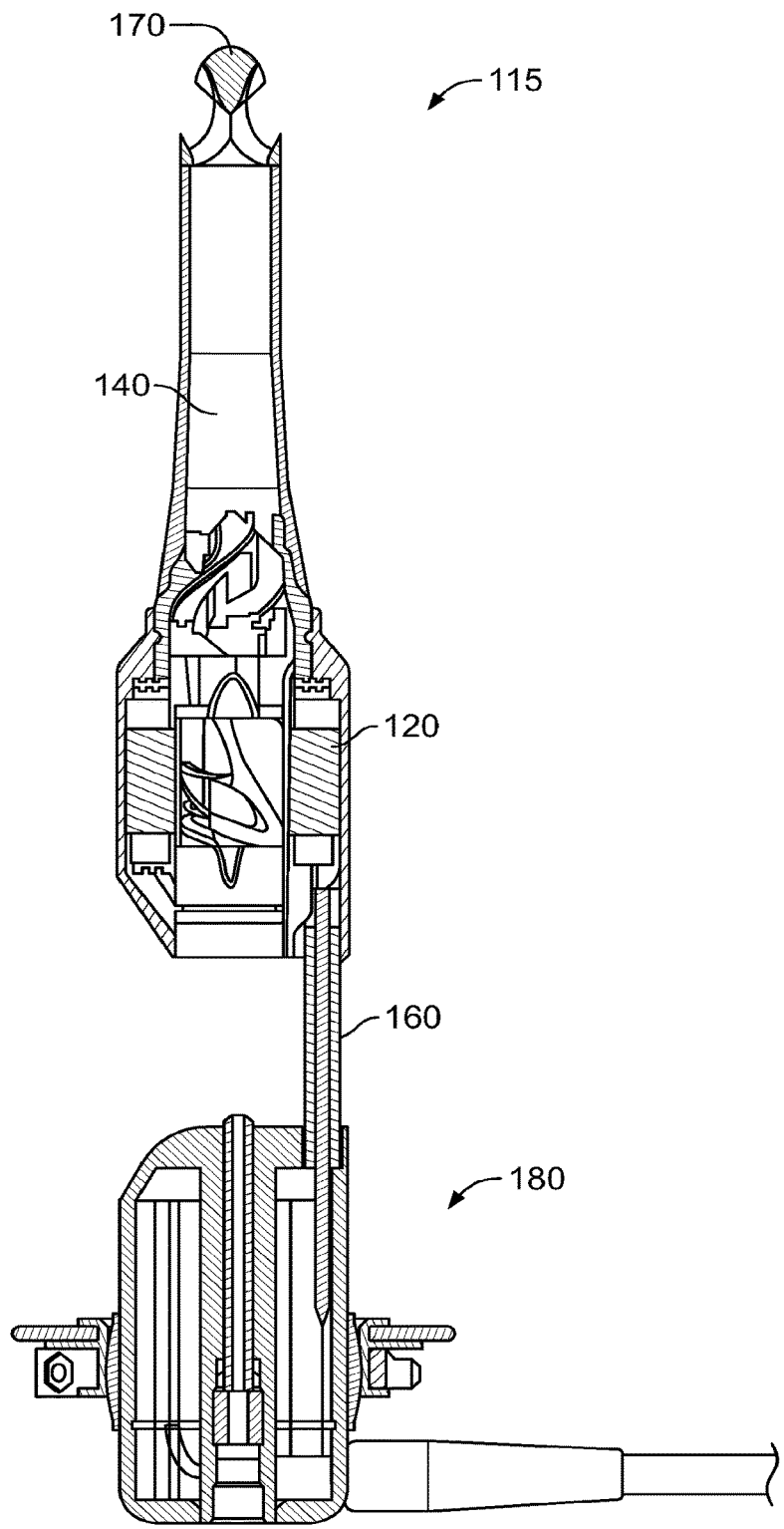
FIG. 6 is a cross-sectional view of the ventricular assist device of FIG. 5.

Certain modifications or additions to VAD 10 may help ensure that heart structures do not get sucked into the pump inlet and that suction conditions do not occur. For example, FIG. 5 illustrates a VAD 115 similar to VAD 10 with certain modifications. VAD 115 may include four sections including a pump 120, an outflow cannula 140, a rigid elongate member 160, and an anchoring element 180. Pump 120 and outflow cannula 140, as well as outflow cannula tip 170, may be identical to pump 20, outflow cannula 40, and outflow cannula tip 70, described in connection with VAD 10. Rigid elongate member 160 may be similar to rigid elongate member 60, with one difference being how rigid elongate member 60 couples to anchor element 180.

Figure 7:
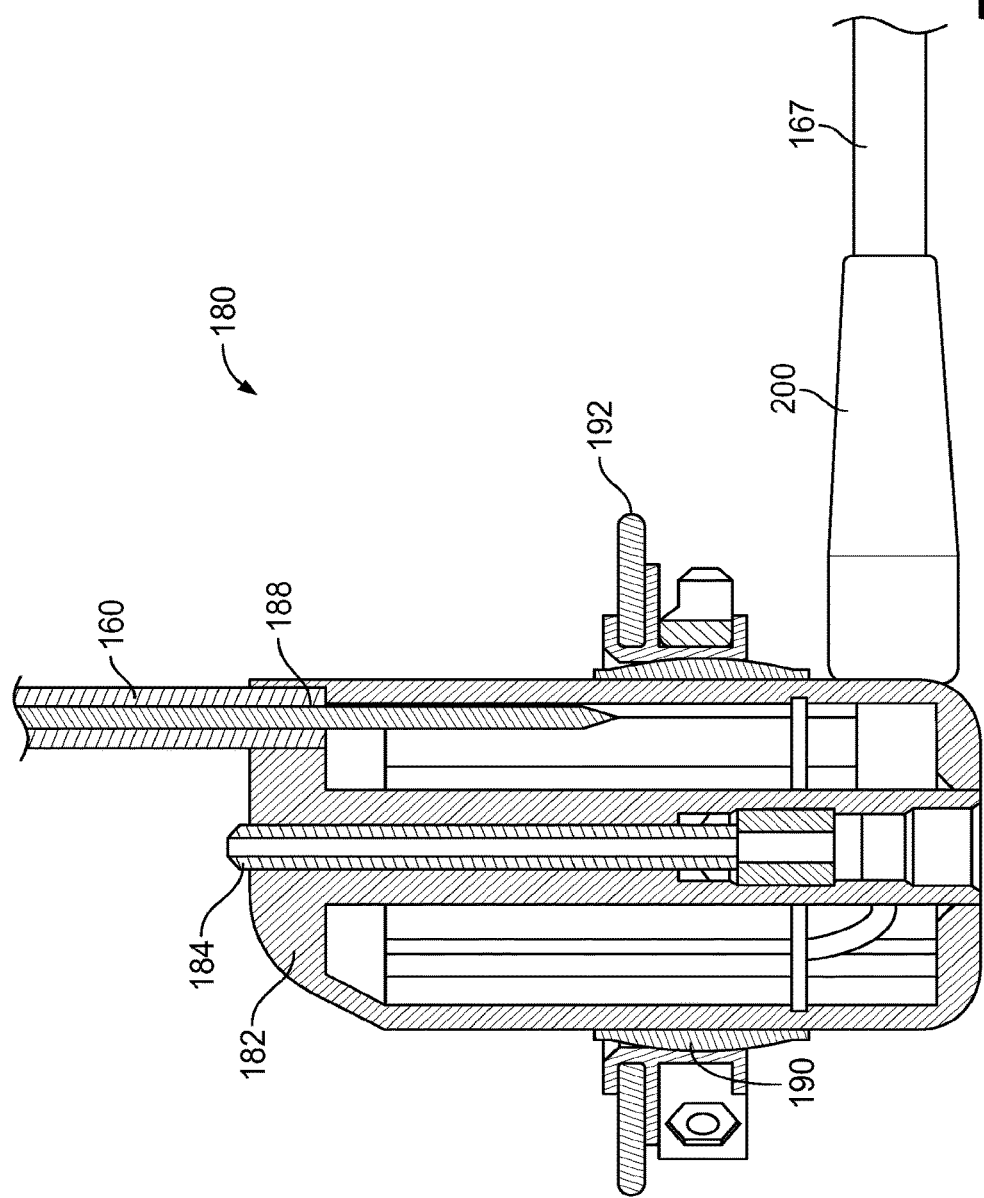
FIG. 7 is an enlarged cross-sectional view of a portion of the device of FIG. 5.

Anchor element 180 is illustrated in greater detail in FIG. 7. Generally, anchor element 180 may include a body 182, illustrated as a substantially cylindrical member in FIG. 7. The body 182 may define a first channel 184 and a second channel 188. The second channel 188 may serve to facilitate coupling rigid elongate member 160 to the anchor element 180, as well as to allow electric wiring 167 to pass from inside rigid elongate member 160 to fitting 200. The function of, and additional structure related to, first channel 184 is described in greater detail below.

Anchor element 180 may also include a ring 192 coupled to body 182 via a spherical element 190. The body 182 may have a length that is substantially greater than the thickness of the ring 192. For example, the length of body 182 may be between about 25 mm and 45 mm, between about 30 mm and 40 mm, or about 35 mm. The thickness of ring 192 may be substantially less than the length of the body 182, and may be, for example, between about 1 mm and 5 mm. It should be understood that these dimensions are merely exemplary and are not intended to limit the scope of the invention. With this configuration, ring 192 and spherical element 190 may slide up or down body 182 when in an unlocked condition, with the ring 192 and spherical element 190 being translationally and rotationally fixed when in a locked condition. The ring 192 may have generally similar structure as ring 80 of VAD 10 and serve a similar function. In other words, during implantation of VAD 115, ring 192 may be mounted to the heart, for example at the apex, to secure anchor element 180 thereto. Spherical element 192 may provide an amount of polyaxial relative motion between body 182 and ring 192 to allow for slight movement of pump 120 via its connection to rigid elongate member 160.

Figure 8:
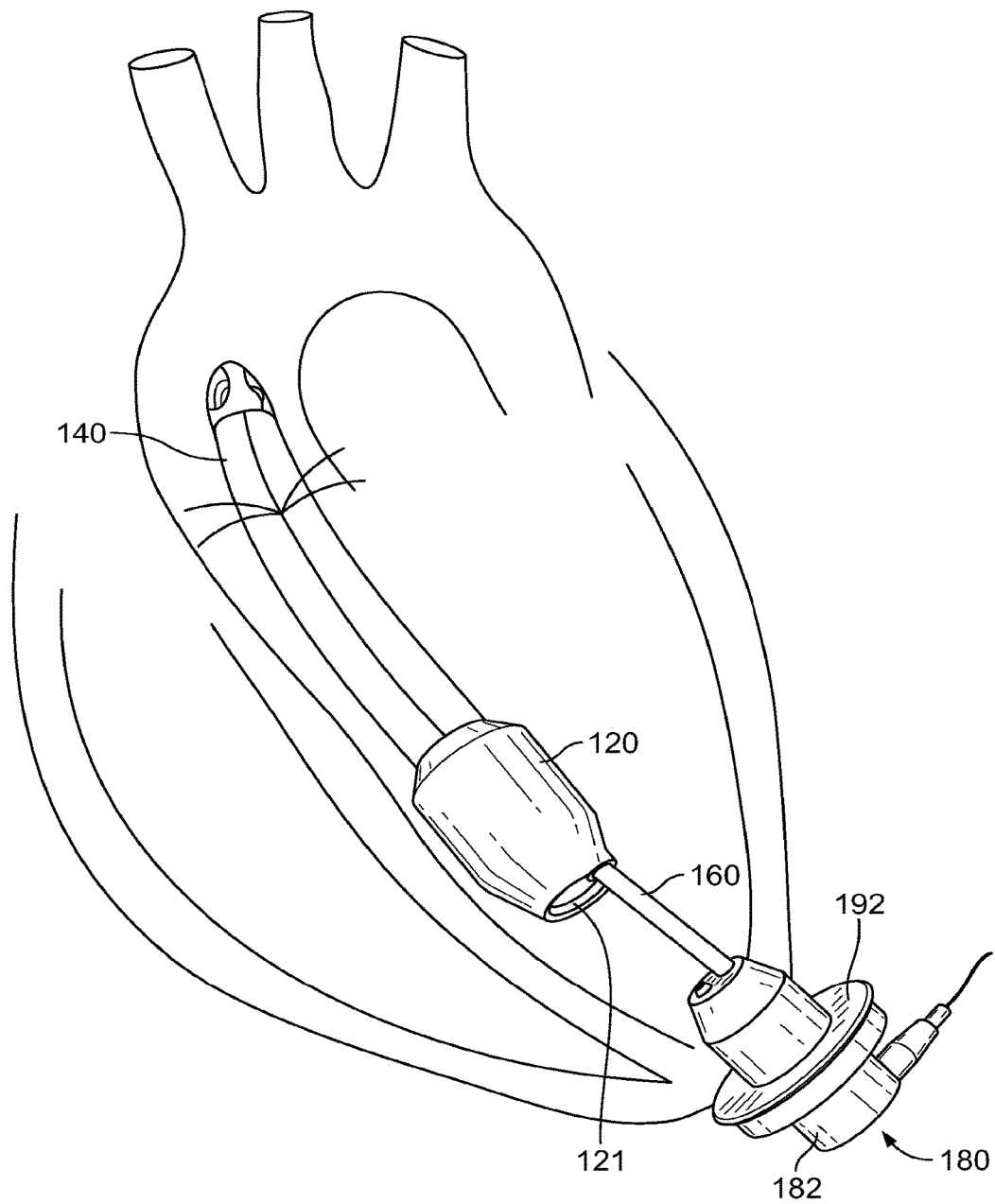
FIG. 8 is a highly schematic view of the device of FIG. 5 in an implanted condition within a heart.

A method of implantation of VAD 115 may be generally similar to the method of implantation of VAD 10 described above. For example, after gaining access to the heart, VAD 115 may be inserted into the heart through a crux incision through the apex of the heart. As illustrated in FIG. 8, pump 120, elongate member 160, and outflow cannula 140 may be inserted through the crux incision and positioned within the left ventricle so that cannula 140 extends through the aortic valve into the aorta with an inlet opening of inlet element 121 of pump 120 positioned within the left ventricle. Prior to securing ring 192 to the apex of the heart, the distance which the VAD 115 extends into the heart may be precisely controlled by changing the distance which the body 182 of anchor element 180 extends into the apex of the heart when the body 182 is in the unlocked condition with respect to ring 192. Once the position of the VAD 115 is suitable, the body 182 and ring 192 may be transitioned into the locked condition to prevent translation of the body 182 with respect to the ring 192, and the ring may be mounted to the heart, for example with sutures.

Once mounted to the heart, the surgeon may utilize first channel 184 of body 182 to perform further procedures in the heart, if desired. For example, as shown in FIG. 9, the surgeon may pass a catheter 300 through first channel 184, including passing the catheter 300 through one-way valve 185 within first channel 184. One-way valve 185 may prevent fluid from exiting the heart through first channel 184 while allowing items to be passed through the channel. For example, valve 185 may be a duckbill valve formed of a resilient material that generally conforms to objects inserted therethrough, providing a fluid tight seal before, during, and after insertion of items through first channel 184. It should be understood that other types of one-way valves may be used as an alternative to a resilient duckbill valve.

Figure 10:
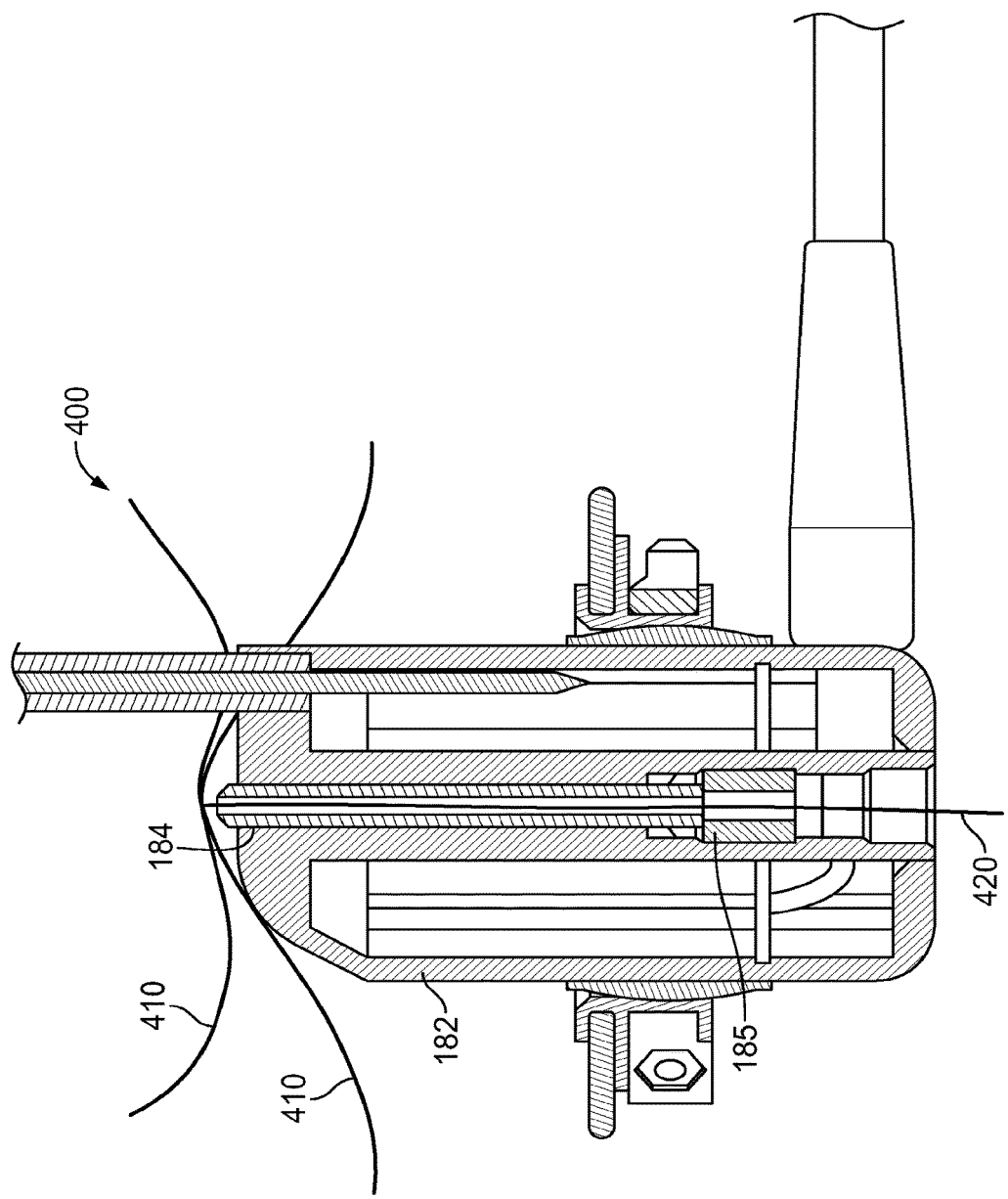
FIG. 10 is an enlarged cross-sectional view of a portion of the device of FIG. 5 with a stent mounted thereto.

In one example, catheter 300 may include one or more inner chambers housing one or more components to be passed through anchor element 180. For example, catheter 300 may house an expandable stent 400 while the stent is in a collapsed condition having a relatively small size compared to the expanded condition. Once at least a portion of the stent 400 is passed through the first channel 184 via the catheter 300, the catheter 300 may be removed or the stent 400 may otherwise be released of the catheter 300 constraining the stent 400. Once the constraint is at least partially removed, stent 400 may transition from the collapsed condition to the expanded condition, for example as illustrated in FIG. 10. The stent 400 may be formed of a superelastic shape-memory alloy, such as Nitinol, or any other suitable expandable and collapsible material. Preferably, stent 400 is self-expandable so that, in the absence of applied force, the stent 400 tends to take a particular pre-set shape which may be set, for example, by heat setting. However, other types of stents, such as balloon expandable stents, may be suitable. For balloon expandable stents, an expandable balloon may be inserted along with a stent surrounding the balloon, with fluid being pumped into the balloon to expand both the balloon and the stent as desired.

Referring still to FIG. 10, the illustrated stent 400 includes a plurality of struts or splines. In particular, the illustrated embodiment includes four struts 410, each strut having an inner end disposed adjacent the inner ends of the other spines and outer ends disposed away from one another when the stent is in the expanded condition. The stent 400 may also include a securing portion 420 to secure the stent 400 to a mounting portion of the VAD 115. As illustrated, securing portion 420 of stent 400 is mounted to anchor element 180. Mounting may be accomplished, for example, via a friction fit between the securing portion 420 of stent 400 and a portion of the anchor element 180, such as the one-way valve 185. Alternatively, other structures may be provided on anchoring element 180, such as clips or retainers, to secure the stent 400. Still further, if a portion of stent 400 extends completely through first channel 184 and outside the heart, other methods such as suturing an end of the stent 400 to the anchoring element 180 may be performed as desired. It should be noted that other components of VAD 115 may serve as the mounting portion for stent 400. For example, stent 400 may be secured to the rigid elongate member 160 and/or a portion of inlet element 121. Still further, it is not strictly necessary for the stent 400 to be mounted to the VAD 115 at all, as long as the stent 400 is secured within the heart. For example, if components of stent 400 are in direct contact with portions of the heart, such as the heart walls, the stent 400 may provide enough radial force to remain substantially stationary without needing to be mounted to the VAD 115.

Figure 11:
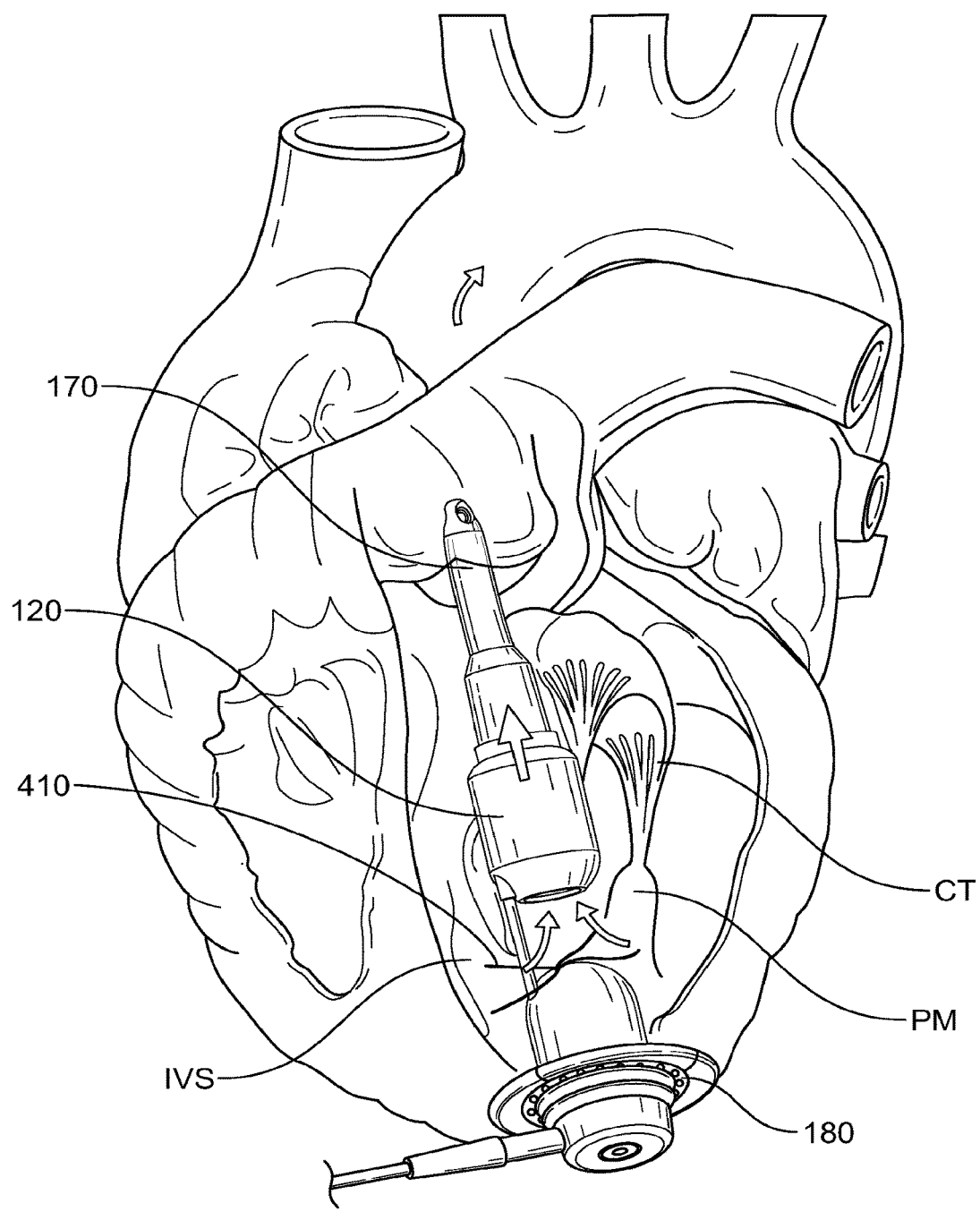
FIG. 11 is a schematic view of the device of FIG. 5 implanted within a heart with a stent mounted to the device.

Proper placement of the VAD 115 and stent 400 may be verified by fluoroscope or other imaging technique. Once proper positioning is confirmed, the surgeon may insert a secondary sealing element into first channel 184, such as a screw or a resilient plug. The secondary sealing member may act as a backup fluid-tight seal to ensure that, in the event one-way valve 185 loses its fluid-tight seal, the first channel 184 remains fluid-tight. One example of possible positioning of the components is illustrated in FIG. 11. As shown here, VAD 115 is positioned with tip 710 on the outflow side of the aortic valve, pump 120 and stent 400 within the left ventricle, and ring 192 of anchor element 180 adjacent the apex of the heart. One or more of the struts 410 of stent 400 may be in contact with and/or adjacent papillary muscles PM, chordae tendinae CT, walls of the heart, the interventricular septum IVS, or other heart structures.

After placement, the pump can be started by applying electrical power from the external or implantable power source, and proper outflow may be verified using echocardiography. After outflow is verified, the crux incision may be closed and the ring 192 secured to the exterior of the cardiac wall. It should be noted that ring 192 may be secured to the heart initially so that the implant process is undertaken with the ring 192 mounted to the heart. Once power is applied and the VAD 115 is in an operating condition, blood is drawn into the inlet opening of inlet element 121, moved through pump 120, and returned to the aorta through the tip 170 of the outlet cannula 140, as indicated by the arrows in FIG. 11. However, as noted above, the low intraventricular pressure caused by the pump 120 drawing blood into the inlet 121 creates the potential for heart anatomy to be sucked into the inlet opening of inlet element 121. As shown in FIG. 11, the struts 410 of stent 400 may act to provide a physical barrier to keep the anatomy, such as the interventricular septum IVS or the ventricle wall, from being able to enter the inlet opening of the inlet element 121. The struts 410 may be in direct contact with the anatomy, providing resistance to the pressure gradient pulling the heart structure toward the inlet 121. Alternatively, the struts 410 may be adjacent the heart structure, such that if the heart structure begins to get pulled toward the inlet 121, the struts 410 provide a barrier to the heart structures being pulled in further. It may be preferable to keep the struts 410 adjacent to, rather than in contact with, the heart structures during normal operating conditions so that they do not otherwise interfere with normal operation of the heart and VAD 115. The stent 400 may also similarly function to prevent tissue from being pulled into the inlet opening of inlet element 121 if the ventricle has relatively little fluid that would lead to a suction condition in the absence of stent 400.

Figure 12:
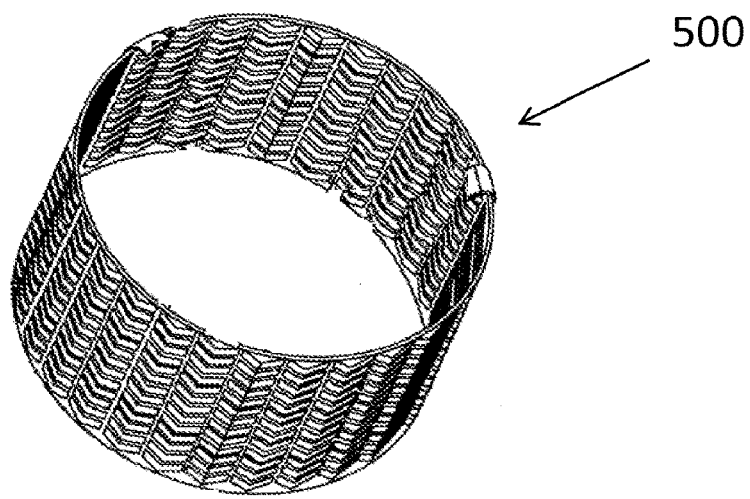
FIG. 12 is a perspective view of a cylindrical stent in an expanded condition.

Although stent 400 is described above as having four struts 410 with inner ends adjacent one another and outer ends spaced apart from one another, the stent 400 may take other suitable forms. For example, a stent similar to stent 400 may be used with any number of struts, including one, two, three, or more than four struts. Further, an alternative stent may take various shapes including circular, cylindrical, or conical when in the expanded condition. Such alternative stents may be laser cut from a single tube of material, for example from a cylinder of Nitinol, or may be formed by braiding material into a mesh. For example, a stent 500 cut from a tube of Nitinol taking the general shape of a cylinder in the expanded condition is illustrated in FIG. 12. Any shape stent that provides a barrier from heart tissue entering the inlet opening of inlet element 121 may be suitable. As noted with stent 400, such stents may be mounted to any portion of VAD 115, such as the anchor element 180, the pump 122, the rigid elongate member 160, or may not be mounted to the VAD 115 at all.

Figure 13:
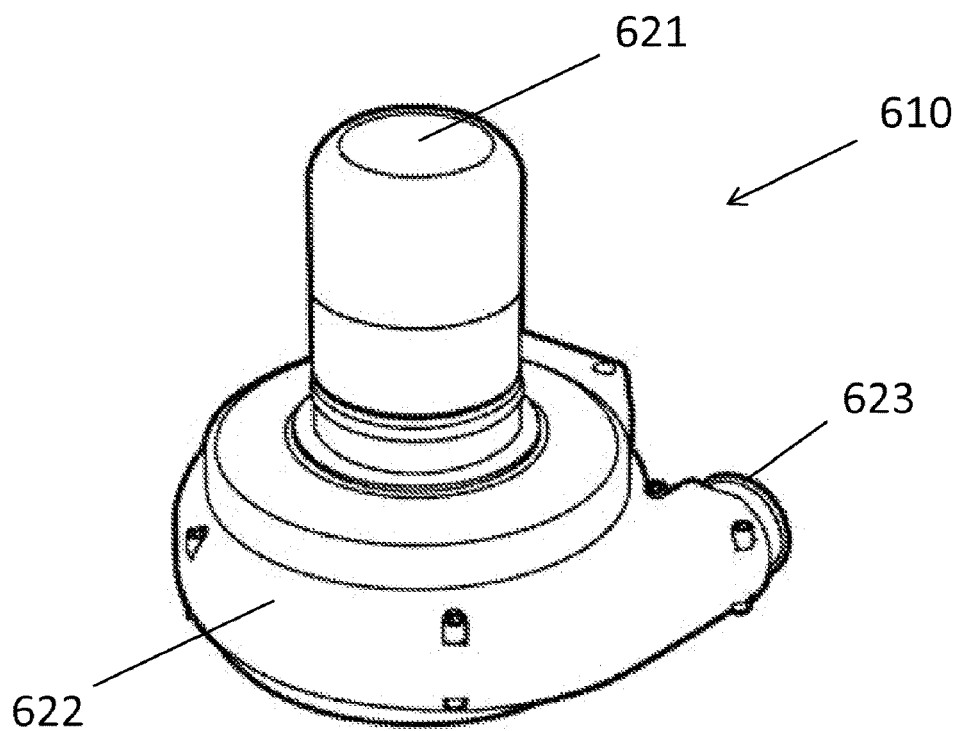
FIG. 13 is a diagrammatic perspective view of another embodiment of a VAD.
Figure 14:
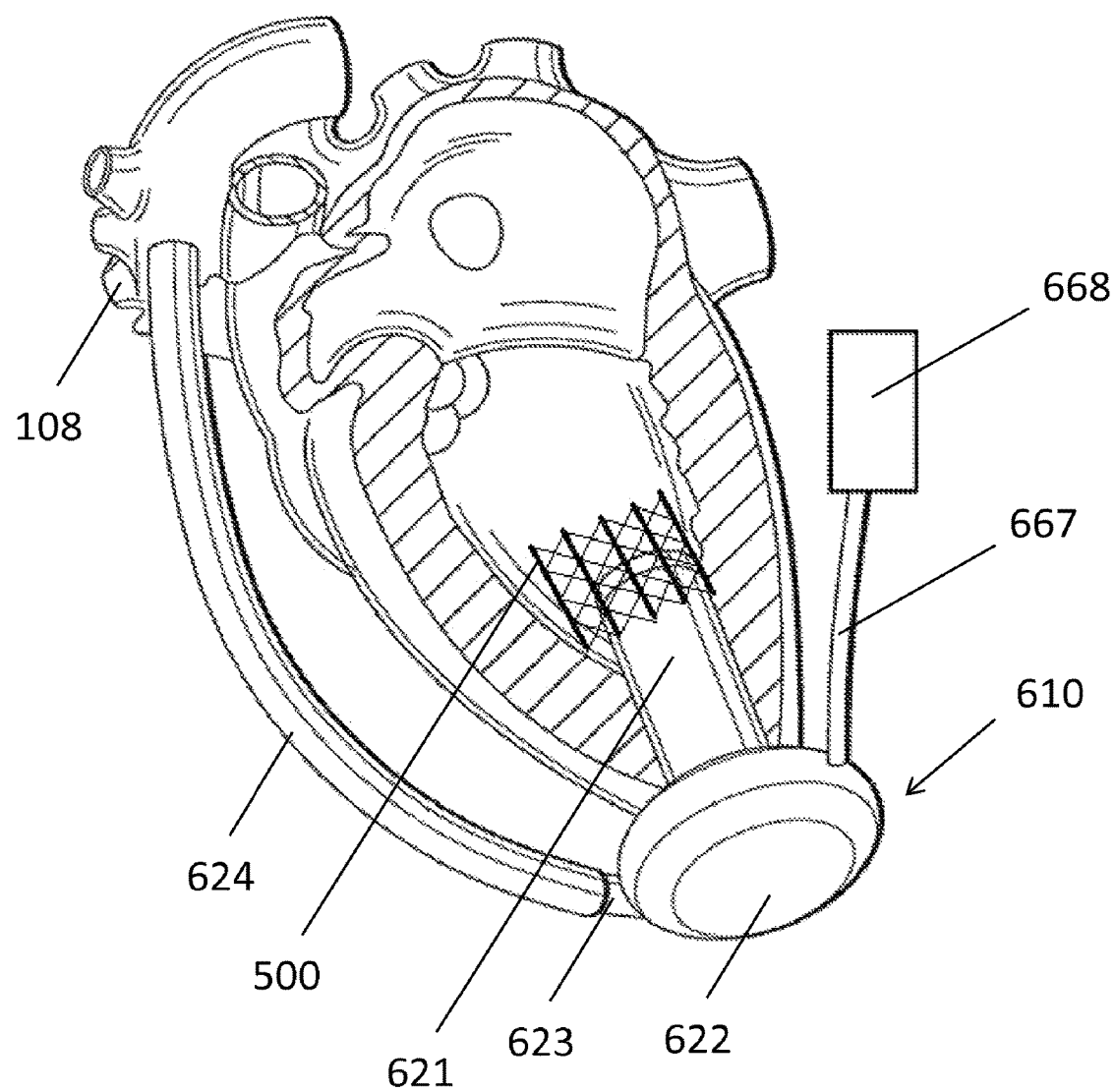
FIG. 14 is a diagrammatic perspective view of the VAD of FIG. 13 and the stent of FIG. 12 implanted into a heart.

Further, although the use of a stent is described above with respect to one particular VAD 115, it should be understood that the concepts described herein may be applied to any heart pump that includes an inlet element defining an inlet opening positioned within a chamber of the heart. For example, FIG. 13 illustrates a different type of VAD 610. Briefly, VAD 610 includes and inlet element 621 having an inlet opening. VAD 610 also includes an outlet port 623. The outlet port 623 may be connected to an outlet cannula, such as a flexible tube 624, that connects to the ascending aorta 108, for example, as shown in FIG. 14. Electrical wiring 667 may operably couple the pump housing 622 to a power source and/or controller 668 which may, for example, be positioned outside the body of the patient. As best illustrated in FIG. 14, VAD 610 may be coupled to the heart so that the pump housing 622 is positioned outside the heart near the apex, with the inlet element 621 being the only portion of the VAD 610 that extends into the ventricle. In this embodiment, a stent such as stent 500 may be mounted to the inlet element 621 and expanded following implantation of the VAD 610 to provide similar function as stent 400. Although not identified, pump housing 622 may include a sealable channel to allow introduction of stent 500 in a collapsed condition through the VAD 610, with the channel being sealed after introduction, expansion, and proper positioning of the stent to ensure the VAD 610 is fluid-tight. As illustrated, stent 500 may be mounted to VAD 610 at least partially upstream of inlet element 621, although stent 500 may alternatively be constrained within the ventricle under its own radial force without the need to mount the stent 500 to the VAD 610. Alternately, the stent may be introduced into the heart prior to the insertion of the inlet element 621 into the heart. In this case, the stent would first expand in the heart and the inlet element 621 would be inserted through the heart and through the inner diameter of the stent. The stent and the inlet element 621 may be provided with mating structures, such as hooks, catches, or other structures, so that inlet element 621 may physically couple to the stent to keep the stent in place. However, such mating structures are optional.

Figure 15:
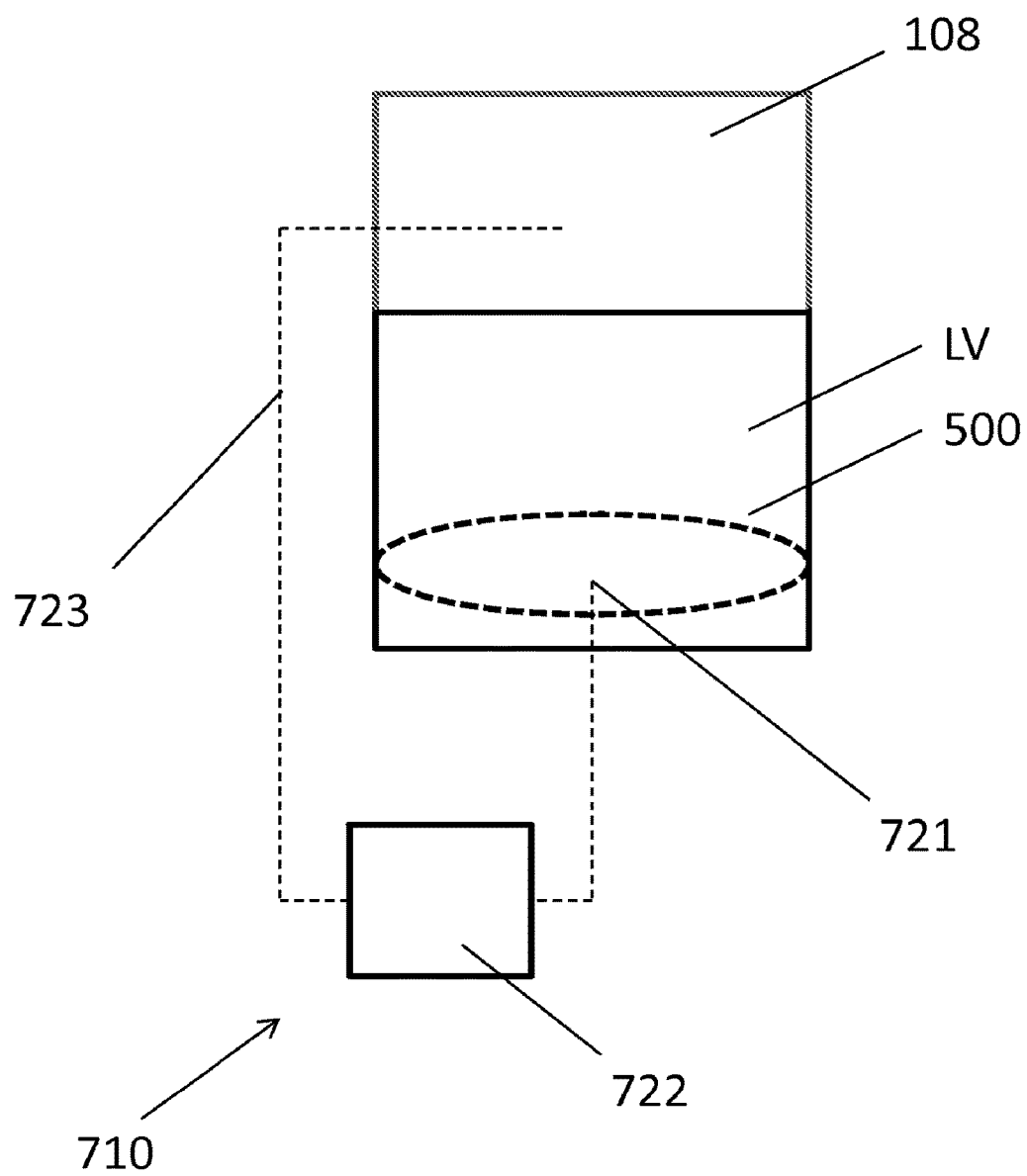
FIG. 15 is a highly schematic representation of a further embodiment of a VAD implanted into a heart with a stent positioned within the heart.

FIG. 15 illustrates a highly schematic VAD 710 implanted within the left ventricle LV. In this embodiment, VAD 710 includes a pump housing 722 remote from the left ventricle. An inlet cannula is connected to the pump housing 722 with an inlet element 721 having an inlet opening positioned within the left ventricle. The inlet element 721 may be a flexible tube, for example, extending through the apex of the heart and mounted thereto. Similarly, VAD 710 may include an outlet cannula 723 extending from the pump housing 722 extending and mounted to the ascending aorta 723. The outlet cannula 723 may also take the form of a flexible tube. A stent, such as stent 500, may be positioned at least partially upstream of the inlet element 721. As in other embodiments, the stent 500 may optionally be mounted to the VAD 710 near the inlet element 121. The stent 500 may be inserted into the left ventricle LV along with, or separately from, inlet element 721, as desired.

As should be clear from the embodiments described above, any VAD having an inlet element with an inlet opening positioned within a ventricle may be used in conjunction with a stent to provide the desired protection from heart structure entering or otherwise interfering with blood flowing into the VAD. As such, the concepts described herein apply to VADs with pumps inside the heart, outside the heart, or mounted to the heart, as well as VADs with outlet cannulas within the heart or remote from the heart.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims. For example, features of any one embodiment described above may be combined with features of other embodiments described above without departing from the scope of the invention.

The invention claimed is:

1. A ventricular assist system, comprising:
a ventricular assist device including a pump and an inlet element defining an inlet opening, the inlet opening being configured to communicate with the pump, the inlet element being adapted for positioning with the inlet opening disposed within a ventricle of a heart when the system is in an operative condition;
an expandable stent adapted for positioning within the ventricle when the system is in the operative condition, the stent including a collapsed condition;
a mounting operably coupled to the pump, the mounting defining a fluid channel configured to extend from a first end outside the ventricle to a second end inside the ventricle;
the stent being configured to pass through the fluid channel in the collapsed condition.

2. The system of claim 1, wherein the mounting is configured to secure a part of the stent in position relative to the inlet element when the stent is positioned within the ventricle.

3. The system of claim 2, wherein the mounting includes an anchor element configured for attachment to the heart and the inlet element and the stent are configured to be secured to the anchor element when the system is in the operative condition.

4. The system of claim 3, wherein the fluid channel extends through the anchor element.

5. The system of claim 4, wherein the fluid channel has a diameter and the stent has the collapsed condition and an expanded condition, the diameter of the channel being adapted to allow the stent to pass through the fluid channel when the stent is in the collapsed condition.

6. The system of claim 5, wherein the anchor element includes a ring.

7. The system of claim 5, wherein the mounting includes a substantially cylindrical member configured to be mounted to the heart at various positions along a length of the substantially cylindrical member.

8. The system of claim 1, further comprising a sealing element configured to be positioned within the fluid channel to seal the fluid channel.

9. The system of claim 1, wherein the stent includes a plurality of struts, each of the plurality of struts having an inner end and an outer end, the inner ends being disposed adjacent one another and the outer ends extending away from one another when the stent is in an expanded condition.

10. The system of claim 1, wherein the stent has the collapsed condition and an expanded condition, the stent being substantially cylindrical when in the expanded condition.

11. The system of claim 1, wherein the stent is formed of a braided mesh.

12. A method of implanting a ventricular assist device in a subject comprising, the method comprising:
implanting the ventricular assist device within the subject;
positioning an inlet opening of an inlet element of the ventricular assist device within a ventricle of the heart, the inlet opening communicating with a pump;
positioning an outflow cannula of the ventricular assist device to communicate with the pump and with an artery;
positioning a stent in the ventricle at least partially upstream of the inlet opening;

positioning a mounting on a proximal end of the ventricular assist device so that the mounting and a channel within the mounting extend across a wall of the ventricle;

passing the stent through the mounting while the stent is in a collapsed condition.

13. The method of claim 12, further comprising operating the pump to draw blood from the ventricle and return the blood to the artery through a heart valve and holding a wall of the ventricle away from the inlet opening with the stent.

14. The method of claim 12, further comprising transitioning the stent from the collapsed condition to an expanded condition.

15. The method of claim 12, further comprising sealing the channel with a sealing element.

\* \* \* \* \*